(12) United States Patent
Lau et al.

(10) Patent No.: US 7,240,353 B2
(45) Date of Patent: Jul. 3, 2007

(54) FUNCTIONALITY RECOMMENDATION SYSTEM

(75) Inventors: Denny W. Lau, Sunnyvale, CA (US); Vijaykalyan Yeluri, Sunnyvale, CA (US); Eric Feingold, Philadelphia, PA (US)

(73) Assignee: General Electric Company, Schenectady, NY (US)

( * ) Notice: Subject to any disclaimer, the term of this patent is extended or adjusted under 35 U.S.C. 154(b) by 234 days.

(21) Appl. No.: 10/996,714

(22) Filed: Nov. 24, 2004

(65) Prior Publication Data

US 2006/0179023 A1    Aug. 10, 2006

(51) Int. Cl.
*G05B 11/01* (2006.01)
*G05B 15/00* (2006.01)
*G06Q 40/00* (2006.01)
*H04N 7/16* (2006.01)
*G06F 7/00* (2006.01)
*G06F 17/30* (2006.01)
*G06F 17/00* (2006.01)

(52) U.S. Cl. ............... 725/24; 705/26; 705/27; 705/37; 700/17; 700/83; 707/2; 707/6; 707/10; 707/104.1; 725/9

(58) Field of Classification Search ........... 705/26–27, 705/37; 700/17, 83; 725/9, 24; 707/2, 6, 707/10, 104.1

See application file for complete search history.

(56) References Cited

U.S. PATENT DOCUMENTS

| 6,064,980 | A | * | 5/2000 | Jacobi et al. ............... 705/26 |
| 6,108,493 | A | * | 8/2000 | Miller et al. ............... 709/219 |
| 6,266,649 | B1 | * | 7/2001 | Linden et al. ............... 705/26 |
| 6,321,221 | B1 | * | 11/2001 | Bieganski ............... 707/5 |
| 6,438,579 | B1 | * | 8/2002 | Hosken ............... 709/206 |
| 6,782,370 | B1 | | 8/2004 | Stack |
| 2002/0186867 | A1 | * | 12/2002 | Gutta et al. ............... 382/116 |

* cited by examiner

*Primary Examiner*—Ronald D Hartman, Jr.
(74) *Attorney, Agent, or Firm*—McAndrews, Held & Malloy, Ltd.; Peter J. Vogel; Michael A. Dellapenna

(57) ABSTRACT

Certain embodiments of the present invention provide a system, method and computer instructions for recommending functionality to users of a system with one or more users. In an embodiment, a functionality recommendation system includes a usage tracking module for tracking usage of functionality by users of a system with one or more users and a recommendation module for: (1) suggesting functionality to users not using the functionality; and/or (2) prompting users of functionality to suggest use of that functionality to users not using the functionality. The functionality recommendation system may also include a recommendation listing module that organizes suggestions, a recommendation output module that outputs suggestions, and/or a functionality tutorial module that outputs information regarding suggested functionality, for example.

23 Claims, 3 Drawing Sheets

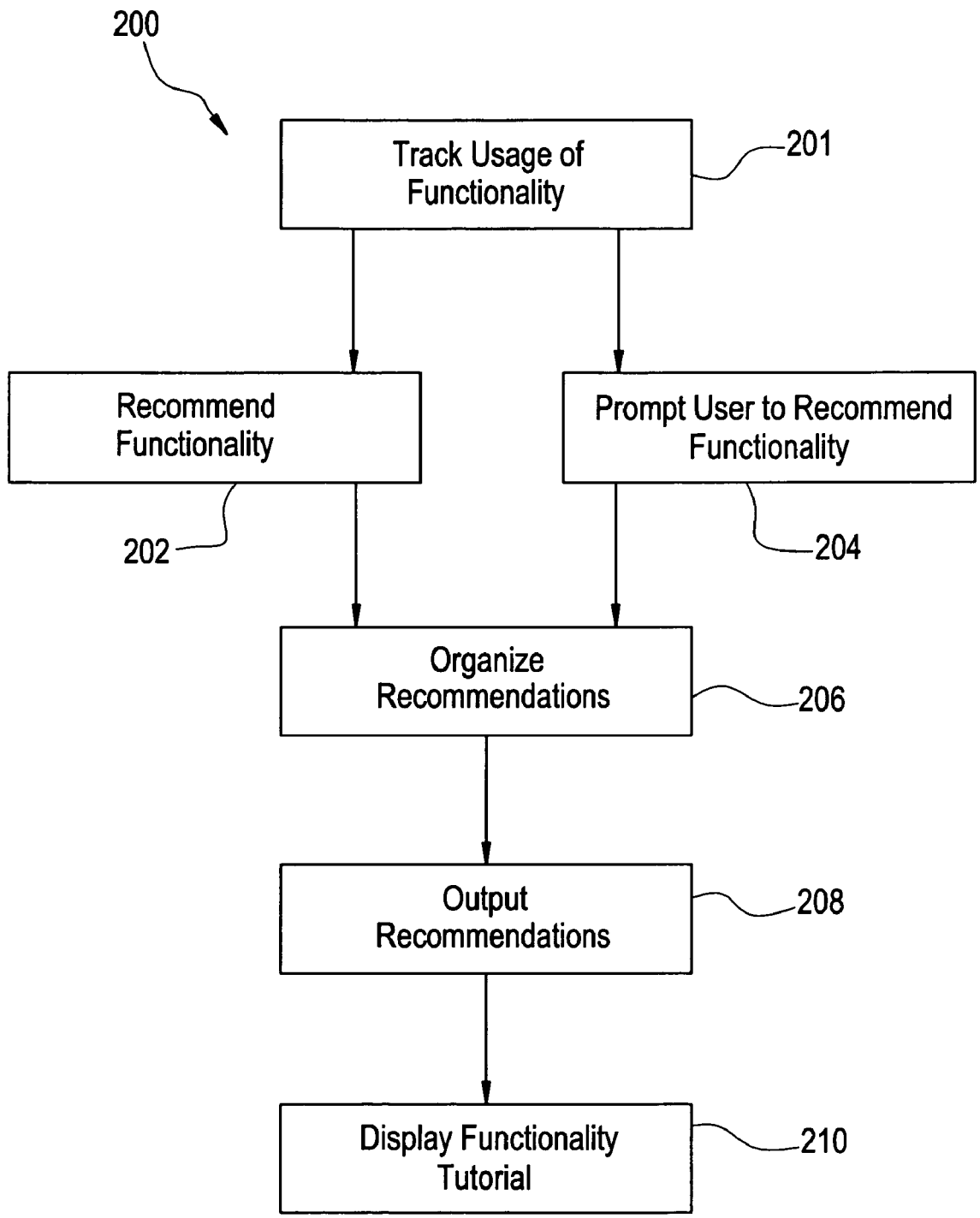

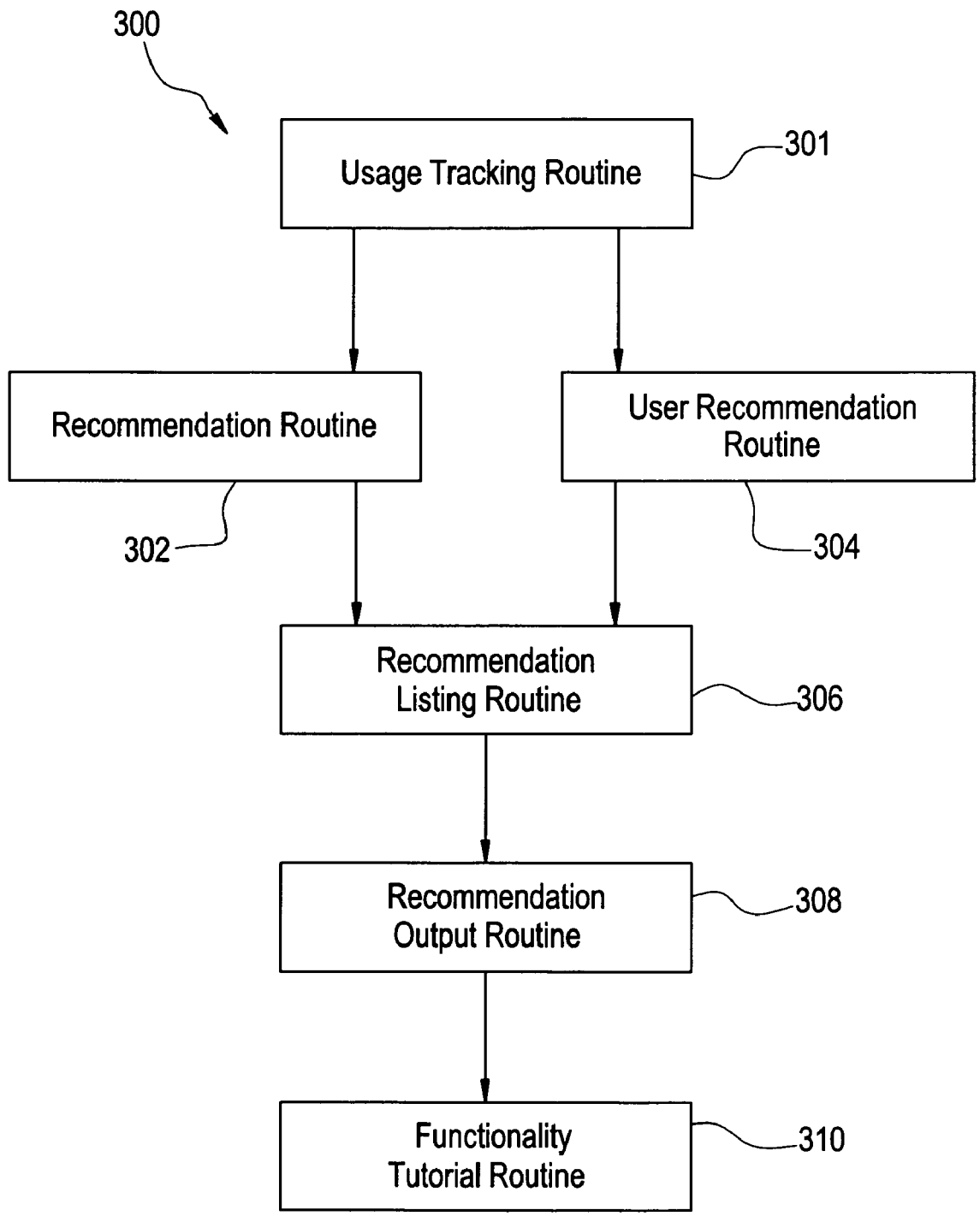

FUNCTIONALITY RECOMMENDATION SYSTEM

RELATED APPLICATIONS

[Not Applicable]

FEDERALLY SPONSORED RESEARCH OR DEVELOPMENT

[Not Applicable]

[MICROFICHE/COPYRIGHT REFERENCE]

[Not Applicable]

BACKGROUND OF THE INVENTION

The present invention generally relates to a system, method and computer instructions for recommending functionality to users of a system with one or more users. More particularly, the present invention relates to a system, method and computer instructions for tracking and suggesting usage of functionality to users of a system with one or more users.

Systems that track usage and then suggest similar products or content to achieve marketing and sales goals are prevalent in numerous industries. In e-commerce applications, product recommendation systems that recommend products similar to a purchased product are common. In entertainment applications, content recommendation systems that recommend content similar to viewed content are common. Tracking usage and then making recommendations based on such usage may also be applied in connection with training users of complex systems.

When a new user is first exposed to a complex system, the user tends to rely upon basic functionalities to accomplish tasks. However, a user that is more experienced with the system may use more advanced functionalities in order to complete the same tasks in a more timely manner. Because many systems are quite complex, the amount of time necessary to bring a new user up to speed with the more senior users may be extensive. Time consuming training cuts the productivity of senior users, making training expensive, but the new users must catch up somehow. Thus, a system, method and computer instructions that reduce a new user's learning curve are highly desirable.

One example of a complex system is a Picture Arching and Communicating System (PACS) workstation used in a clinical care setting. The PACS workstation is used by a community of users that perform similar tasks. Unfortunately, the PACS workstation is somewhat intolerant of mistakes, which inhibits new users from experimenting with different functionalities. Thus, new PACS workstation users often develop a habit of using only basic functionalities to complete tasks.

Although many tasks may be completed using basic functionalities, the same tasks may often be completed in a more timely manner by utilizing advanced and/or streamlined functionalities. Failure to realize when advanced and/or streamlined functionalities are available may cause new PACS workstation users to spend more time on tasks than experienced PACS workstation users, creating a disparity in efficiency between the two types of users.

In order for the new PACS workstation users to catch up with the experienced users, one-on-one training and/or time consuming experimentation is often required, which are inefficient ways to bring new PACS workstation users up to speed. One way to decrease the disparity in efficiency between experienced PACS workstation users and new PACS workstation users is to incorporate customized training into the system itself. Therefore, a functionality recommendation system that diminishes the learning curve for new PACS workstation users and ensures that all new users receive training on the same functionalities is highly desirable.

Thus, there is a need for an improved functionality recommendation system, method and computer instructions.

BRIEF SUMMARY OF THE INVENTION

Certain embodiments of the present invention provide a system, method and computer instructions for recommending functionality to users of a system with one or more users. In an embodiment, a functionality recommendation system includes a usage tracking module for tracking usage of functionality by users of the system and a recommendation module for: (1) suggesting functionality to users not using the functionality; and/or (2) prompting users of functionality to suggest use of that functionality to users not using the functionality. The functionality recommendation system may also include a recommendation listing module that organizes suggestions, a recommendation output module that outputs suggestions, and/or a functionality tutorial module that outputs information regarding suggested functionality, for example.

In an embodiment, a method for recommending functionality includes tracking usage of functionality by users of a system with one or more users and recommending functionality to users not using the functionality and/or prompting users of functionality to suggest that functionality to users not using the functionality. The method for recommending functionality may also include organizing recommendations, outputting recommendations and/or outputting information regarding recommended functionality, for example.

In an embodiment, a computer-readable storage medium includes a set of instructions for a computer directed to recommending functionality to users of a system with one or more users. The set of instructions includes a usage tracking routine for tracking usage of functionality by users of the system and a recommendation routine for: (1) suggesting functionality to users not using the functionality; and/or (2) prompting users of functionality to suggest use of that functionality to users not using the functionality. The set of instructions may also include a recommendation listing routine that organizes suggestions, a recommendation output routine that outputs suggestions, and/or a functionality tutorial routine that outputs information regarding suggested functionality, for example.

These and other features of the present invention are discussed or apparent in the following detailed description of certain embodiments of the invention.

BRIEF DESCRIPTION OF THE DRAWINGS

FIG. 2 illustrates a flow diagram for a method for recommending functionality used in accordance with an embodiment of the present invention.

FIG. 3 illustrates a set of computer instructions for recommending functionality used in accordance with an embodiment of the present invention.

Figure 1:
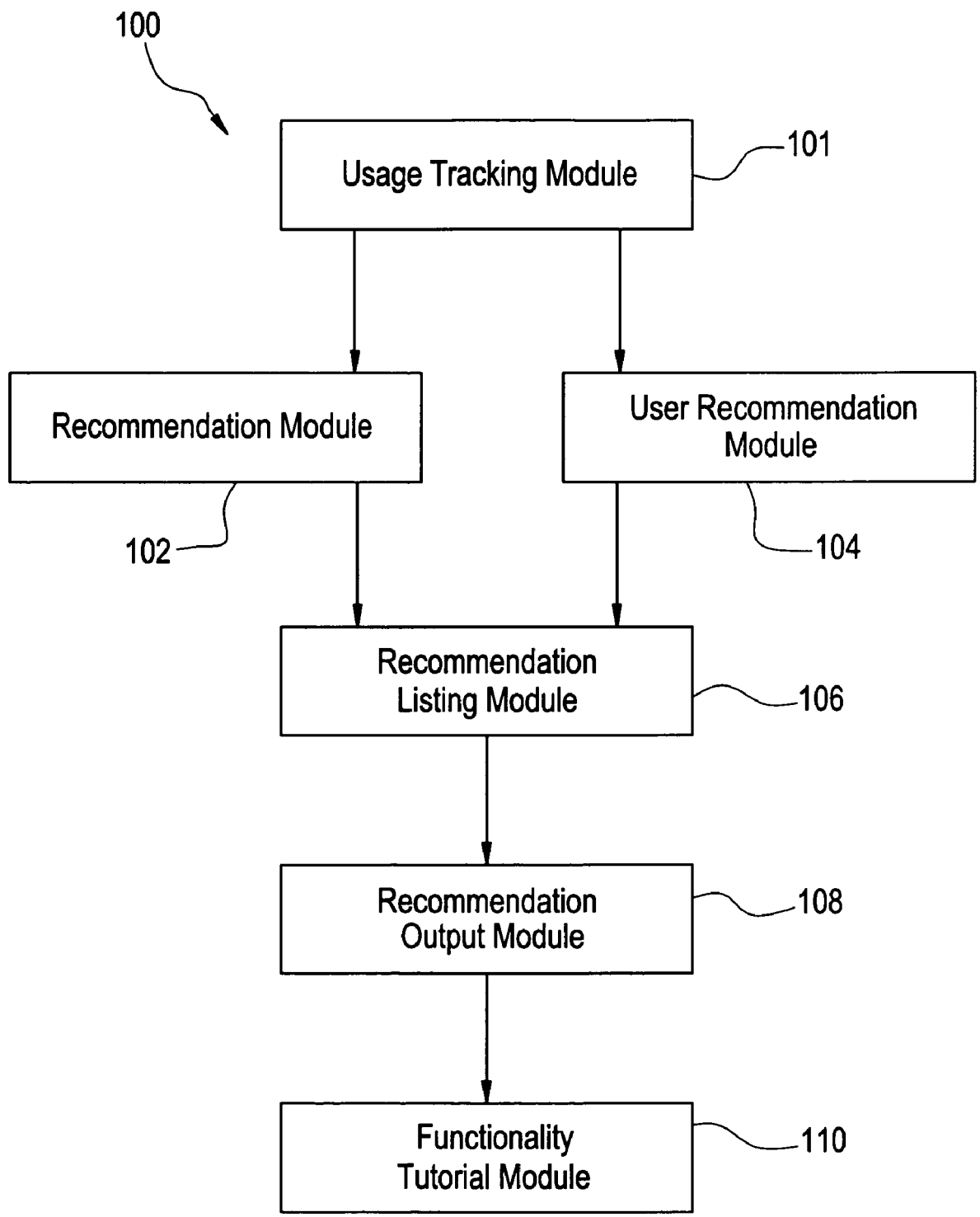
FIG. 1 illustrates a functionality recommendation system used in accordance with an embodiment of the present invention.

The foregoing summary, as well as the following detailed description of embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF CERTAIN EMBODIMENTS

FIG. 1 illustrates a functionality recommendation system 100 for recommending functionality to users of a system with one or more users used in accordance with an embodiment of the present invention. The functionality recommendation system 100 includes a usage tracking module 101, a recommendation module 102, a user recommendation module 104, a recommendation listing module 106, a recommendation output module 108 and a functionality tutorial module 110. The components of the system 100 may be implemented in many ways. For example, the components may be implemented in hardware and/or software. The components may be implemented separately and/or integrated in various combinations. Other desirable ways to implement the components of the system 100 may exist.

In the functionality recommendation system 100, the usage tracking module 101 tracks usage of functionality by users of a system with one or more users. Then, based on the usage of functionality, the recommendation module 102 suggests functionality to users not using the functionality and/or the user recommendation module 104 prompts users of functionality to suggest use of that functionality to users not using the functionality. Suggestions generated by the recommendation module 102 and/or the user recommendation module 104 may be organized by the recommendation listing module 106. The suggestions may be output by the recommendation output module 108. A functionality tutorial module 110 may output information regarding the suggested functionality.

In the functionality recommendation system 100, the usage tracking module 101 tracks usage of functionality by users of a system with one or more users. The usage tracking module 101 may be configurable. For example, the usage tracking module 101 may be configured to track usage of functionality by users that are members of a certain user group. The usage tracking module 101 may also be configured to track usage of functionality by all users of the system. The usage tracking module 101 may be configured such that new user groups may be added and existing user groups may be deleted. The usage tracking module 101 may also be configured such that users may be tracked as members of multiple user groups or members of no user group at all. Other desirable ways to configure the usage tracking module 101 may exist.

In the functionality recommendation system 100, the recommendation module 102 suggests functionality to users not using the functionality. The recommendation module 102 may be configurable. For example, the recommendation module 102 may be configured to suggest functionality to users not using the functionality when a configurable percentage of users of the system use the functionality. For example, the recommendation module 102 may be configured to suggest functionality to users not using a functionality when fifty percent of users use the functionality. Other desirable ways to configure the recommendation module 102 may exist.

In the functionality recommendation system 100, the user recommendation module 104 prompts users of functionality to suggest use of that functionality to users not using the functionality. The user recommendation module 104 may be configurable. For example, the user recommendation module 104 may be configured to prompt users of functionality to suggest use of that functionality to users not using the functionality when a configurable percentage of users of the system do not use the functionality. For example, the user recommendation module 104 may be configured to prompt users of a functionality to suggest the functionality to users not using the functionality when eighty percent of users do not use the functionality. Other desirable ways to configure the user recommendation module 104 may exist.

Users of functionality that are prompted by the user recommendation module 104 to suggest functionality to users not using the functionality may choose not to suggest the functionality. In an embodiment, the user recommendation module 104 may be configured to suggest functionality to users not using the functionality when a user prompted by the user recommendation module 104 chooses not to suggest the functionality to users not using the functionality.

In an embodiment, the recommendation module 102 and the user recommendation module 104 may be combined into a single module. For example, the recommendation module 102 and the user recommendation module 104 may be combined into a single module that: (1) suggests functionality to users not using the functionality; and/or (2) prompts users of functionality to suggest use of that functionality to users not using the functionality.

In the functionality recommendation system 100, the recommendation listing module 106 organizes suggestions generated by the recommendation module 102 and/or the user recommendation module 104. The recommendation listing module 106 may be configured to organize suggestions in many ways. For example, the recommendation listing module 106 may be configured to organize suggestions based on a difference between a number of users of a system using a functionality and a number of users of the system not using the functionality. The recommendation listing module 106 may also be configured to organize suggestions based on a priority level assigned to a user making a suggestion, and/or a priority level assigned to a functionality, for example. The priority level may be assigned by an administrator of the system and/or by a user receiving a suggestion. Other desirable ways to configure the recommendation listing module 106 to organize suggestions may exist.

In the functionality recommendation system 100, the recommendation output module 108 outputs suggestions generated by the recommendation module 102 and/or the user recommendation module 104. The recommendation output module 108 may be configured to output suggestions in many ways. For example, the recommendation output module 108 may be configured to output suggestions in an order based on whether the suggestion was generated by the recommendation module 102 or the user recommendation module 104. In this example, suggestions generated by the recommendation module 102 may be listed ahead of suggestions generated by the user recommendation module 104 or vice versa. The recommendation output module 108 may also be configured to output suggestions such that the suggestions generated by the recommendation module 102 are output separately from the recommendations generated by the user recommendation module 104. In an embodiment that includes both a recommendation listing module 106 and a recommendation output module 108, the recommendation output module 108 may be configured to output suggestions in the same order that the recommendation listing module 106 organizes the suggestions. Suggestions may also be output based on a priority level assigned to the suggestions by a user(s) and/or the system 100. Other desirable ways to configure the recommendation output module 108 to output suggestions may exist.

As well as outputting suggestions generated by the recommendation module 102 and/or the user recommendation module 104, the recommendation output module 108 may be configured to output other information. For example, the recommendation output module 108 may be configured to output: a name for a suggested functionality; the user that suggested the functionality (if the suggestion was generated by the user recommendation module 104); which user group(s) received the suggestion; the percentage of users from each user group(s) using the suggested functionality; and/or the percentage of users from each user group(s) not using the suggested functionality. It may be desirable for the recommendation output module 108 to output other information.

Suggestions and other information output by the recommendation output module 108 may be output in many ways. For example, the output may be a visual display, an audio display, printed matter, a facsimile transmission, and/or electronic mail. Other desirable ways for the recommendation output module 108 to output suggestions and other information may exist.

In the functionality recommendation system 100, the functionality tutorial module 110 outputs information regarding functionality that has been suggested by the recommendation module 102 and/or the user recommendation module 104. The functionality tutorial module 110 may be configured to output information regarding suggested functionality in many different ways. For example, the functionality tutorial module 110 may be configured to output information when the recommendation module 102 suggests functionality. The functionality tutorial module 110 may also be configured to output information when the user prompted by the user recommendation module 104 chooses to suggest the functionality. The functionality tutorial module 110 may be configured to output information when the user prompted by the user recommendation module 104 chooses not to suggest the functionality. In an embodiment that includes both a recommendation output module 108 and a functionality tutorial module 110, the functionality tutorial module 110 may be configured to output information with the output generated by the recommendation output module 108. Further, in an embodiment that includes both a recommendation output module 108 and a functionality tutorial module 110, the information output by the functionality tutorial module 110 may be accessible from the output generated by the recommendation output module 108 even though the information output by the functionality tutorial module 110 is not output with the output generated by the recommendation output module 108. Other desirable ways to configure the functionality tutorial module 110 to output information regarding suggested functionality may exist.

Information output by the functionality tutorial module 110 may be output in many ways. For example, the output may be a visual display, an audio display, printed matter, a facsimile transmission, and/or electronic mail. Other desirable ways for the functionality tutorial module 110 to output information may exist.

The functionality recommendation system 100 may be configurable. For example, a user may indicate that a suggested functionality is not useful so that the functionality will not be suggested again to that user. Further, a user may block all future suggestions from a specified user or user group, or block functionality suggestions altogether. Other desirable ways to configure the functionality recommendation system 100 may exist.

In operation, the functionality recommendation system 100 is used in connection with a system with one or more users. The functionality recommendation system 100 first tracks usage of functionality by users of the system. For example, the usage tracking module 101 uses a counter to track a number of users of a certain functionality and/or a number of users of the system not using the functionality. Then, the system 100 determines that users not using functionality should use the functionality and/or that users of functionality should be prompted to suggest use of that functionality to users of the system not using the functionality. For example, if use of a functionality exceeds a certain threshold, use of the functionality is suggested to users of the system not using the functionality. In another example, if non-use of a functionality dips below a certain threshold, users of the functionality are prompted to suggest use of that functionality to users of the system not using the functionality. The functionality recommendation system 100 may organize suggestions. For example, a functionality with a higher disparity between the percent of users using the functionality and the percent of users not using the functionality may be listed ahead of a functionality with a lower disparity between the percent of users using the functionality and the percent of users not using the functionality. The functionality recommendation system 100 may output suggestions that users of the system not using functionalities use the functionalities. For example, a graphical listing of suggested functionalities may be displayed to users of the system not using the functionalities. The functionality recommendation system 100 may output a functionality tutorial to users of the system not using suggested functionalities. For example, a graphical display of images, video and/or text to show how to use suggested functionalities may be displayed.

The functionality recommendation system 100 may be used in connection with any type of system with one or more users. For example, the functionality recommendation system 100 may be used in connection with a medical system and/or a clinical care system.

FIG. 2 illustrates a flow diagram for a method for recommending functionality 200 used in accordance with embodiments of the present invention. At 201, usage of functionality by users of a system with one or more users is tracked. For example, a table stores functionality used by users of a system such as a PACS system or other information system. Each functionality in the table may be associated with a counter value. The counter value for a functionality may be increased each time a user uses the functionality. At 202, functionality is suggested to a user not using the functionality. For example, if the counter value for a functionality exceeds a threshold value, the functionality is suggested to users not using the functionality. At 204, a user of functionality is prompted to suggest that functionality to a user not using the functionality. For example, if the counter value for a functionality exceeds a threshold value, users of the functionality are prompted to suggest that functionality to users not using the functionality. At 206, suggestions generated by steps 202 and/or 204 are organized. For example, suggestions may be organized based on the counter value, a priority level assigned to the functionality and/or a priority level assigned to the user suggesting the functionality. At 208, suggestions generated by steps 202 and/or 204 are output. For example, suggestions may be output as a visual display, an audio display, printed matter, a facsimile transmission, and/or electronic mail. At 210, a functionality tutorial that contains information regarding functionality suggested in steps 202 and/or 204 is output. In an embodiment, suggestions output at 208 may not be accompanied by a tutorial at 210.

The method for recommending functionality 200 may be applied in a medical setting, a clinical care setting or any other setting where a system with one or more users is used. For example, a PACS workstation is a system with one or more users used in the clinical care setting by medical personnel to complete certain tasks. For example, radiologists use PACS workstations to view images of different types of anatomy. In order to optimally view a certain type of anatomy, certain window and level settings are required. To find the optimal window and level settings, new radiologists often use multiple functions. For example, new radiologists select tools from a tool palette and then adjust window and level settings manually to find the optimal setting. However, PACS workstations have a single function that optimizes window and level settings based on the type of anatomy being viewed. More experienced radiologists use the optimization function to optimize window and level settings automatically.

Utilizing the method for recommending functionality 200 described above may be beneficial in this scenario. First, usage of functionality by all radiologists is tracked. Then, suggestions to use the optimization function are made to radiologists not using the optimization function and/or radiologists using the optimization function are prompted to suggest use of the optimization function to radiologists not using the optimization function. Suggestions may then be organized and/or output to radiologists not using the optimization function. A functionality tutorial for the optimization function may be output.

FIG. 3 illustrates a set of computer instructions for recommending functionality 300 used in accordance with an embodiment of the present invention. The set of computer instructions for recommending functionality 300 includes a usage tracking routine 301, a recommendation routine 302, a user recommendation routine 304, a recommendation listing routine 306, a recommendation output routine 308 and a functionality tutorial routine 310.

In the set of computer instructions for recommending functionality 300, the usage tracking routine 301 tracks usage of functionality by users. Then, based on the usage of functionality, the recommendation routine 302 suggests functionality to users not using the functionality and/or the user recommendation routine 304 prompts users of functionality to suggest use of that functionality to users not using the functionality. Suggestions generated by the recommendation routine 302 and/or the user recommendation routine 304 are organized by the recommendation listing routine 306. The suggestions are output by the recommendation output routine 308. A functionality tutorial routine 310 outputs information regarding the suggested functionality.

In an embodiment, the usage tracking routine 301, the recommendation routine 302, the user recommendation routine 304, the recommendation listing routine 306, recommendation output routine 308, and the functionality tutorial routine 310, may perform functions similar to the usage tracking module 101, the recommendation module 102, the user recommendation module 104, the recommendation listing module 106, the recommendation output module 108, and the functionality tutorial module 110, respectively, as described above in relation to FIG. 1.

The set of computer instructions for recommending functionality 300 may be used in connection with any type of system with one or more users. For example, the set of computer instructions for recommending functionality 300 may be used in connection with a medical system and/or a clinical care system.

While the invention has been described with reference to embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A functionality recommendation system comprising:
a usage tracking module comprising a table and a counter, wherein said table includes an entry for a functionality available on a picture arching and communicating system workstation, and wherein said counter tracks the usage of said functionality by a user group; and
a recommendation module capable of suggesting that one or more non-users of said functionality use said functionality based on said usage,
wherein said recommendation module suggests said functionality to one or more non-users when at least a configurable percentage of said user group use said functionality, and
wherein said recommendation module does not suggest said functionality to one or more non-users when the percentage of said user group that use said functionality is less than said configurable percentage.

2. The system of claim 1, further comprising a recommendation listing module that organizes suggestions generated by said recommendation module.

3. The system of claim 1, further comprising a recommendation output module that outputs one or more suggestions generated by said recommendation module.

4. The system of claim 1, further comprising a functionality tutorial module that outputs information regarding said functionality.

5. A method for recommending a functionality comprising:
tracking usage of a functionality available on a picture arching and communicating system workstation by one or more members of a user group;
when at least a configurable percentage of said user group use said functionality, suggesting said functionality to one or more members of said user group that do not use said functionality;
when the percentage of said user group that use said functionality is less than the configurable percentage. not suggesting said functionality to one or more members of said user group that do not use said functionality.

6. The method of claim 5, further comprising outputting one or more suggestions to one or more members of said user group.

7. The method of claim 5, further comprising outputting a functionality tutorial that contains information regarding said functionality to one or more members of said user group.

8. A computer-readable storage medium including a set of instructions for a computer, the set of instructions comprising:
- a usage tracking routine for tracking usage of a functionality available on a picture arching and communicating system workstation by a user group; and
- a recommendation routine for suggesting one or more non-users of said functionality use said functionality based on said usage,
- wherein said recommendation routine suggests said functionality to one or more non-users when at least a configurable percentage of said user group use said functionality, and
- wherein said recommendation routine does not suggest said functionality to one or more non-users when the percentage of said user group that use said functionality is less than the configurable percentage.

9. The set of instructions of claim 8, further comprising a recommendation listing routine for organizing suggestions generated by said recommendation routine.

10. The set of instructions of claim 8, further comprising a recommendation output routine for outputting one or more suggestions generated by said recommendation routine.

11. The set of instructions of claim 8, further comprising a functionality tutorial routine for outputting information regarding said functionality.

12. A functionality recommendation system comprising:
- a usage tracking module comprising a table and a counter, wherein said table includes an entry for a functionality and said counter tracks the usage of said functionality by a user group; and
- a recommendation module capable of prompting one or more users of said functionality to suggest that one or more non-users of said functionality use said functionality based on said usage,
- wherein said recommendation module prompts said one or more users to suggest said functionality to said one or more non-users when at least a configurable percentage of said user group does not use said functionality, and
- wherein said recommendation module does not prompt said one or more users to suggest said functionality to said one or more non-users when the percentage of said user group that does not use said functionality is less than the configurable percentage.

13. The system of claim 12, further comprising a recommendation listing module that organizes suggestions generated by said recommendation module.

14. The system of claim 12, further comprising a recommendation output module that outputs one or more suggestions generated by said recommendation module.

15. The system of claim 12, further comprising a functionality tutorial module that outputs information regarding said functionality.

16. The system of claim 12, wherein said functionality is available on a picture arching and communicating system workstation.

17. A method for recommending a functionality comprising:
- tracking usage of a functionality by one or more members of a user group;
- when at least a configurable percentage of said user group does not use said functionality, prompting one or more members of said user group that use said functionality to suggest said functionality to one or more members of said user group that do not use said functionality; and
- when the percentage of said user group that does not use said functionality is less than the configurable percentage, not prompting one or more members of said user group that use said functionality to suggest said functionality to one or more members of said user group that do not use said functionality.

18. The method of claim 17, further comprising outputting one or more suggestions to one or more members of said user group.

19. The method of claim 17, further comprising outputting a functionality tutorial that contains information regarding said functionality to one or more members of said user group.

20. A computer-readable storage medium including a set of instructions for a computer, the set of instructions comprising:
- a usage tracking routine for tracking usage of a functionality by a user group; and
- a recommendation routine for prompting one or more users of said functionality to suggest that one or more non-users of said functionality use said functionality based on said usage,
- wherein said recommendation routine prompts said one or more users to suggest said functionality to said one or more non-users when at least a configurable percentage of said user group does not use said functionality, and
- wherein said recommendation routine does not prompt said one or more users to suggest said functionality to said one or more non-users when the percentage of said user group that does not use said functionality is less than the configurable percentage.

21. The set of instructions of claim 20, further comprising a recommendation listing routine for organizing suggestions generated by said recommendation routine.

22. The set of instructions of claim 20, further comprising a recommendation output routine for outputting one or more suggestions generated by said recommendation routine.

23. The set of instructions of claim 20, further comprising a functionality tutorial routine for outputting information regarding said functionality.

* * * * *